United States Patent
Yatcilla et al.

(10) Patent No.: US 7,329,419 B2
(45) Date of Patent: Feb. 12, 2008

(54) HERBAL SUPPLEMENT TO SUPPORT WEIGHT LOSS

(75) Inventors: Michael Yatcilla, Los Angeles, CA (US); Kim Krumhar, Carlsbad, CA (US); Janice Thompson, Rancho Santa Fe, CA (US)

(73) Assignee: Herbalife International, Inc., Los Angeles, CA (US)

( * ) Notice: Subject to any disclaimer, the term of this patent is extended or adjusted under 35 U.S.C. 154(b) by 0 days.

(21) Appl. No.: 11/233,782

(22) Filed: Sep. 22, 2005

(65) Prior Publication Data

US 2006/0165820 A1  Jul. 27, 2006

Related U.S. Application Data

(60) Provisional application No. 60/612,426, filed on Sep. 23, 2004.

(51) Int. Cl.
*A61K 36/00* (2006.01)
(52) U.S. Cl. .................................. 424/725
(58) Field of Classification Search ............ None
See application file for complete search history.

(56) References Cited

U.S. PATENT DOCUMENTS

2001/0008641 A1 * 7/2001 Krotzer ................. 424/725
2002/0164387 A1 11/2002 Wei et al.
2004/0077556 A1 4/2004 Chinery
2005/0085454 A1 * 4/2005 Ghosal ................. 514/185

OTHER PUBLICATIONS

Anonymous. "Xenadrine EFX; Product Profile (More Info)." Internet Article, 'Online!' Aug. 6, 2004. URL: http://web.archive.org/web/20040806054855/http://www.cytodynecom/products.html>Retrieved on Jan. 26, 2006.
Anonymous. "Xenadrine NRG; Product Profile (More Info)." Internet Article, 'Online!' Aug. 6, 2004. URL: http://web.archive.org/web/20040806054855/http://www.cytodyne.com/products.html>Retrieved on Jan. 26, 2006.
Nasir et al. "Exercise-induced syncope associated with QT prolongation and ephedra-free Xenadrine." *Mayo Clinic Proceedings 2004*. 79(8):1059-1062 (2004).
Saldana et al. "Extraction of Purine Alkaloids from Mate (Ilex paraguariensis) Using Supercritical C02." *Journal of Agricultural and Food Chemistry*. 47(9):3804-3808 (1999).

* cited by examiner

*Primary Examiner*—Christopher R. Tate
*Assistant Examiner*—Deborah A. Davis
(74) *Attorney, Agent, or Firm*—Knobbe, Martens, Olson & Bear LLP

(57) ABSTRACT

Disclosed herein are herbal and chemical combinations for promoting weight loss. The herbs in the composition can include, among others, green tea, ginger, cocoa, and yerba mate. Other chemicals in the composition can include, among others, caffeine and a pharmaceutically acceptable salt of calcium.

21 Claims, No Drawings

HERBAL SUPPLEMENT TO SUPPORT WEIGHT LOSS

RELATED APPLICATIONS

This application is a non-provisional application, and claims priority to the U.S. Provisional Patent Application Ser. No. 60/612,426, filed on Sep. 23, 2004, by Yatcilla et al., and entitled "HERBAL SUPPLEMENT TO SUPPORT WEIGHT LOSS," the disclosure of which is incorporated by reference herein in its entirety, including any drawings.

BACKGROUND OF THE INVENTION

1. Field of the Invention

The present invention relates to pharmaceuticals and herbal supplements. More particularly, the present invention relates to combinations of herbal and other chemical ingredients useful in effecting weight loss.

2. Description of the Related Art

Obesity and an increasingly overweight population are a continuing problem among the American public. To combat this problem, many diets, exercise programs, pharmaceuticals, and herbal supplements have been developed. In the past, one series of herbal supplements in common use contained the drug ephedra. Such supplements were promoted as aiding weight loss, enhancing sports performance, and increasing energy. Due in part to perceived adverse side effects, the FDA has recommended that the public stop using ephedra-containing supplements. Thus, there is a heightened need for alternative herbal supplements that may promote weight loss and increase energy without the adverse effects now associated with ephedra-containing supplements.

SUMMARY OF THE INVENTION

One aspect of the present invention is a tablet comprising green tea, ginger, caffeine, cocoa, and yerba maté.

One aspect of the present invention is a tablet comprising green tea, ginger, caffeine, cocoa, yerba maté, and calcium.

Another aspect of the present invention is a tablet comprising epigallocatechin-3-gallate, caffeine, theobromine, gingerols, and yerba maté.

Another aspect of the present invention is a tablet comprising green tea, ginger, caffeine, cocoa, calcium, yerba maté, hawthorne berry, parsley leaf, marshmallow root, fennel seed, astragalus root, licorice root, suma, cinnamon, celery seed, and alfalfa leaf.

Another aspect of the present invention is a tablet comprising green tea, ginger, caffeine, cocoa, and yerba maté wherein between 25% and 75% of active ingredients are green tea, between 10% and 30% of active ingredients are ginger, between 5% and 25% of active ingredients are caffeine, between 2% and 20% of active ingredients are cocoa, and between 2% and 20% of active ingredients are yerba maté.

Another aspect of the present invention is a tablet comprising green tea, ginger, caffeine, cocoa, yerba maté, and calcium wherein between 20% and 45% of active ingredients are green tea extract, between 10% and 30% of active ingredients are ginger extract, between 5% and 20% of active ingredients are cocoa extract, between 5% and 20% of active ingredients are yerba mate extract, between 5% and 25% of active ingredients are caffeine, and between 5% and 20% of active ingredients are calcium.

Another aspect of the present invention is a tablet comprising green tea, ginger, caffeine, cocoa, calcium, yerba maté, hawthorne berry, parsley leaf, marshmallow root, fennel seed, astragalus root, licorice root, suma, cinnamon, celery seed, and alfalfa leaf, wherein between 10% and 40% of active ingredients are green tea, between 5% and 25% of active ingredients are ginger, between 1% and 20% of active ingredients are caffeine, between 1% and 20% of active ingredients are cocoa, between 10% and 30% of active ingredients are calcium, between 1% and 20% of active ingredients are yerba mate, between 0.1% and 5% of active ingredients are hawthorne berry, between 0.1% and 5% of active ingredients are parsley leaf, between 0.1% and 5% of active ingredients are marshmallow root, between 0.1% and 5% of active ingredients are fennel seed, between 0.1% and 5% of active ingredients are astragalus root, between 0.1% and 5% of active ingredients are licorice root, between 0.1% and 5% of active ingredients are suma, between 0.1% and 5% of active ingredients are cinnamon, between 0.1% and 5% of active ingredients are celery seed, and between 0.1% and 5% of active ingredients are alfalfa leaf.

DETAILED DESCRIPTION OF THE PREFERRED EMBODIMENT

In some embodiments, compositions are provided that include non-ephedra-containing herbal components or extracts and/or other chemical compounds. In some embodiments, these compositions promote weight loss when administered to a mammal, such as a human. In some embodiments, these compositions increase energy when administered to a mammal, such as a human. In some embodiments, these compositions increase the metabolic rate of a mammal, such as a human when administered to the mammal. In some embodiments, these compositions increase thermogenesis when administered to a mammal, such as a human. In some embodiments, these compositions decrease cravings for food when administered to a mammal, such as a human. In some embodiments, these compositions are particularly useful for males. In some embodiments, these compositions are particularly useful for females.

In other embodiments, methods are provided for promoting weight loss, increasing energy, increasing metabolic rate, increasing thermogenesis, and/or decreasing cravings for food by administering the compositions disclosed herein.

Active Ingredients—Herbal Sources

In some embodiments, green tea may be included in the compositions disclosed herein. In one embodiment, the green tea is included as Tier I Green Tea Extract, which contains 50% epigallocatechin-3-gallate (EGCG). EGCG increases metabolism by approximately 5% compared to control. EGCG lowers the respiratory quotient, thereby increasing the metabolic oxidation of fat. Catechins, such as those found in green tea, have also been associated with decreased rates of certain cancers. The green tea extract may comprise from between 3% and 80% of the total active ingredients. In some embodiments, the green tea extract is between 5% and 60% of the total active ingredients. In some embodiments, the green tea extract is between 10% and 50% of the total active ingredients. In some embodiments, the green tea extract is between 20% and 40% of the total active ingredients. In some embodiments, the green tea extract is between 25% and 30% of the total active ingredients.

In some embodiments, ginger may be included in the compositions disclosed herein. In some embodiments, the ginger is included as ginger extract that contains between 1% and 20% gingerol content. In one embodiment, the ginger extract contains 6% gingerols. Gingerols are a carminative that calms the stomach and have been shown in animal studies to increase energy expenditure (metabolic rate) in muscle tissues. The ginger extract may comprise from between 1% and 80% of the total active ingredients. In some embodiments, the ginger extract is between 3% and 60% of the total active ingredients. In some embodiments, the ginger extract is between 5% and 40% of the total active ingredients. In some embodiments, the ginger extract is between 8% and 30% of the total active ingredients. In some embodiments, the ginger extract is between 10% and 20% of the total active ingredients.

In some embodiments, cocoa may be included in the compositions disclosed herein. In one embodiment, the cocoa is an extract from *Theobroma cacao* seeds. In one embodiment, the extract contains 6% theobromine. Theobromine boosts metabolism without simultaneously stimulating the central nervous system. The cocoa extract may comprise from between 1% and 50% of the total active ingredients. In some embodiments, the cocoa extract is between 2% and 40% of the total active ingredients. In some embodiments, the cocoa extract is between 3% and 25% of the total active ingredients. In some embodiments, the cocoa extract is between 4% and 15% of the total active ingredients. In some embodiments, the cocoa extract is between 4% and 10% of the total active ingredients.

In some embodiments, Yerba Maté (*Ilex paraguarensis*) may be included in the compositions disclosed herein. In one embodiment, the Yerba Maté is included as an extract from *Ilex paraguarensis* leaves. Yerba Maté contains caffeine and is a stimulant. In some embodiments, the Yerba Maté extract contains 8% caffeine. The Yerba Maté extract may comprise from between 1% and 50% of the total active ingredients. In some embodiments, the Yerba Maté extract is between 2% and 40% of the total active ingredients. In some embodiments, the Yerba Maté extract is between 3% and 25% of the total active ingredients. In some embodiments, the Yerba Maté extract is between 4% and 15% of the total active ingredients. In some embodiments, the Yerba Maté extract is between 4% and 10% of the total active ingredients.

In some embodiments, celery may be included in the compositions disclosed herein. In one embodiment, celery is included as a dried powder of celery seeds. The celery may comprise from between 0.1% and 20% of the total active ingredients. In some embodiments, the celery is between 0.2% and 10% of the total active ingredients. In some embodiments, the celery is between 0.4% and 5% of the total active ingredients. In some embodiments, the celery is between 0.6% and 3% of the total active ingredients. In some embodiments, the celery is between 1% and 2% of the total active ingredients.

In some embodiments, Hawthorne berry may be included in the compositions disclosed herein. In one embodiment, Hawthorne berry is included as a dried powder. Hawthorn berry powder has antioxidant properties and is known to offer benefits to the health and function of the human heart, helping to reduce the incidence of necrosis of heart tissue and thereby improve cardiac efficiency. The Hawthorne berry may comprise from between 0.1% and 20% of the total active ingredients. In some embodiments, the Hawthorne berry is between 0.2% and 10% of the total active ingredients. In some embodiments, the Hawthorne berry is between 0.4% and 5% of the total active ingredients. In some embodiments, the Hawthorne berry is between 0.6% and 3% of the total active ingredients. In some embodiments, the Hawthorne berry is between 1% and 2% of the total active ingredients.

In some embodiments, parsley may be included in the compositions disclosed herein. In one embodiment, celery is included as a dried powder of parsley leaves. The parsley may comprise from between 0.1% and 20% of the total active ingredients. In some embodiments, the parsley is between 0.2% and 10% of the total active ingredients. In some embodiments, the parsley is between 0.4% and 5% of the total active ingredients. In some embodiments, the parsley is between 0.6% and 3% of the total active ingredients. In some embodiments, the parsley is between 1% and 2% of the total active ingredients.

In some embodiments, marshmallow (*Althaea officinalis*) may be included in the compositions disclosed herein. In one embodiment, marshmallow is included as a dried powder of marshmallow roots. The marshmallow may comprise from between 0.1% and 20% of the total active ingredients. In some embodiments, the marshmallow is between 0.2% and 10% of the total active ingredients. In some embodiments, the marshmallow is between 0.4% and 5% of the total active ingredients. In some embodiments, the marshmallow is between 0.6% and 3% of the total active ingredients. In some embodiments, the marshmallow is between 1% and 2% of the total active ingredients.

In some embodiments, fennel may be included in the compositions disclosed herein. In one embodiment, fennel is included as a dried powder of fennel seeds. The fennel may comprise from between 0.1% and 20% of the total active ingredients. In some embodiments, the fennel is between 0.2% and 10% of the total active ingredients. In some embodiments, the fennel is between 0.4% and 5% of the total active ingredients. In some embodiments, the fennel is between 0.6% and 3% of the total active ingredients. In some embodiments, the fennel is between 1% and 2% of the total active ingredients.

In some embodiments, astragalus may be included in the compositions disclosed herein. In one embodiment, astragalus is included as a dried powder of astragalus roots. The astragalus may comprise from between 0.1% and 20% of the total active ingredients. In some embodiments, the astragalus is between 0.2% and 10% of the total active ingredients. In some embodiments, the astragalus is between 0.4% and 5% of the total active ingredients. In some embodiments, the astragalus is between 0.6% and 3% of the total active ingredients. In some embodiments, the astragalus is between 1% and 2% of the total active ingredients.

In some embodiments, licorice may be included in the compositions disclosed herein. In one embodiment, licorice is included as a dried powder of licorice roots. The licorice may comprise from between 0.1% and 20% of the total active ingredients. In some embodiments, the licorice is between 0.2% and 10% of the total active ingredients. In some embodiments, the licorice is between 0.4% and 5% of the total active ingredients. In some embodiments, the licorice is between 0.6% and 3% of the total active ingredients. In some embodiments, the licorice is between 1% and 2% of the total active ingredients.

In some embodiments, suma (*Pfaffia paniculata*) may be included in the compositions disclosed herein. In one embodiment, suma is included as a dried powder of suma roots. The suma may comprise from between 0.1% and 20% of the total active ingredients. In some embodiments, the suma is between 0.2% and 10% of the total active ingredients. In some embodiments, the suma is between 0.4% and 5% of the total active ingredients. In some embodiments, the suma is between 0.6% and 3% of the total active ingredients. In some embodiments, the suma is between 1% and 2% of the total active ingredients.

In some embodiments, cinnamon may be included in the compositions disclosed herein. In one embodiment, cinnamon is included as a dried extract of cinnamon bark. The cinnamon may comprise from between 0.1% and 20% of the total active ingredients. In some embodiments, the cinnamon is between 0.2% and 10% of the total active ingredients. In some embodiments, the cinnamon is between 0.3% and 5% of the total active ingredients. In some embodiments, the cinnamon is between 0.4% and 2% of the total active ingredients. In some embodiments, the cinnamon is between 0.5% and 1% of the total active ingredients.

In some embodiments, alfalfa may be included in the compositions disclosed herein. In one embodiment, alfalfa is included as alfalfa leaves. The alfalfa may comprise from between 0.01% and 20% of the total active ingredients. In some embodiments, the alfalfa is between 0.03% and 10% of the total active ingredients. In some embodiments, the alfalfa is between 0.05% and 5% of the total active ingredients. In some embodiments, the alfalfa is between 0.1% and 2% of the total active ingredients. In some embodiments, the alfalfa is between 0.15% and 0.5% of the total active ingredients.

Active Ingredients—Chemical Compounds

In some embodiments, calcium may be included in the compositions disclosed herein. The calcium may be included as any pharmaceutically acceptable salt of calcium. In one embodiment, calcium is included as calcium carbonate. Calcium is known to lower the absorption of dietary fat by complexing with fatty acids during the digestive process to form insoluble, indigestible soaps that are then eliminated from the body. Certain calcium salts such as calcium carbonate are also useful excipients and aid in tableting. The calcium may comprise from between 1% and 50% of the total active ingredients. In some embodiments, the calcium is between 2% and 40% of the total active ingredients. In some embodiments, the calcium is between 3% and 25% of the total active ingredients. In some embodiments, the calcium is between 4% and 15% of the total active ingredients. In some embodiments, the calcium is between 5% and 10% of the total active ingredients.

In some embodiments, caffeine may be included in the compositions disclosed herein. In one embodiment, caffeine is included as anhydrous powder. Caffeine acts on the central nervous system to increase alertness, muscular activity, and fatty acid released for metabolism and production of cellular energy. The caffeine may comprise from between 1% and 50% of the total active ingredients. In some embodiments, the caffeine is between 2% and 40% of the total active ingredients. In some embodiments, the caffeine is between 3% and 25% of the total active ingredients. In some embodiments, the caffeine is between 4% and 20% of the total active ingredients. In some embodiments, the caffeine is between 5% and 15% of the total active ingredients.

Combinations of Active Ingredients

In some embodiments, compositions are provided that comprise mixtures of some or all of the active ingredients described above. In some embodiments, compositions are provided that comprise green tea extract, ginger extract, and caffeine. In some embodiments, the foregoing composition comprises between 20% and 65% of the total active ingredients as green tea extract, between 10% and 40% of the total active ingredients as ginger extract, and between 5% and 35% of the total active ingredients as caffeine. In some embodiments, the ingredients of this composition work together synergistically to increase overall metabolic rate and oxidation of fat for energy in cells. In some embodiments, this composition provides a 5% daily increase in metabolic energy expenditure (e.g., between 80-100 Kcals per day).

In some embodiments, compositions are provided that comprise green tea, ginger, cocoa, and yerba mate. In some embodiments, the foregoing composition comprises between 20% and 45% of the total active ingredients as green tea extract, between 10% and 30% of the total active ingredients as ginger extract, between 5% and 20% of the total active ingredients as cocoa extract, and between 5% and 20% of the total active ingredients as yerba mate extract.

In some embodiments, compositions are provided that comprise green tea, ginger, caffeine, cocoa, and yerba mate. In some embodiments, the foregoing composition comprises between 25% and 75% of active ingredients as green tea, between 10% and 30% of active ingredients as ginger, between 5% and 25% of active ingredients as caffeine, between 2% and 20% of active ingredients as cocoa, and between 2% and 20% of active ingredients as yerba maté.

In some embodiments, compositions are provided that comprise green tea, ginger, caffeine, cocoa, calcium, and yerba mate. In some embodiments, the foregoing composition comprises between 20% and 45% of the total active ingredients as green tea extract, between 10% and 30% of the total active ingredients as ginger extract, between 5% and 20% of the total active ingredients as cocoa extract, between 5% and 20% of the total active ingredients as yerba mate extract, between 5% and 25% of the total active ingredients as caffeine, and between 5% and 20% of the total active ingredients as calcium.

In some embodiments, pharmaceutical compositions are provided that comprise a mixture of epigallocatechin-3-gallate, caffeine, and gingerols. In some embodiments, pharmaceutical compositions are provided that comprise a mixture of epigallocatechin-3-gallate, theobromine, gingerols, and caffeine. In some embodiments, pharmaceutical compositions are provided that comprise a mixture of epigallocatechin-3-gallate, theobromine, gingerols, caffeine, and calcium.

In various embodiments, any of the compositions described above may include one or more ingredients selected from the group consisting of Hawthorne berry, parsley leaf, marshmallow root, fennel seed, astragalus root, licorice root, suma, cinnamon, celery seed, and alfalfa leaf.

Pharmaceutical Compositions

In some embodiments, the active ingredients and mixtures of active ingredients may be used, for example, in pharmaceutical compositions comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

Compositions of the active ingredients may be formulated and used as tablets, capsules, or elixirs for oral administration; suppositories for rectal administration; sterile solutions, suspensions for injectable administration; patches for transdermal administration, and sub-dermal deposits and the like. Injectables can be prepared. in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection. The active ingredients can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical formulations for parenteral administration include aqueous solutions of the active ingredients in water-soluble form. Additionally, suspensions of the active ingredients may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the ingredients to allow for the preparation of highly concentrated solutions.

Pharmaceutical preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. Such formulations can be made using methods known in the art. See, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The pharmaceutical compositions may be manufactured in a manner that is itself known, for example, by means of conventional mixing, dissolving, granulating, dragee-making, levitating, emulsifying, encapsulating, entrapping, or lyophilizing processes.

To formulate the dosage including one or more active ingredients disclosed herein, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing ingredients, sweeteners, fragrances, colorants, preservatives and the like may be added to the administered formulation of the compound of the invention, particularly when the compound is to be administered orally.

Further disclosed herein are various pharmaceutical compositions well known in the pharmaceutical art for uses that include intraocular, intranasal, and intraauricular delivery. Pharmaceutical formulations include aqueous ophthalmic solutions of the active ingredients in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions described herein may be administered by either oral or a non-oral pathways. When administered orally, compositions can be administered in capsule, tablet, granule, spray, syrup, or other such form. Compositions also may be brewed, as with a tea, or formed by dissolving a powdered composition into a fluid, typically water, fruit or vegetable juice, or milk. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the ingredients of the invention into optimal contact with living tissue.

Agents intended to be administered intracellularly may be administered using techniques well known to those of ordinary skill in the art. For example, such agents may be encapsulated into liposomes, then administered by any of the methods described herein. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

In some embodiments, the compositions described herein are formulated into a single pill or tablet. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

Methods of Administration

Some embodiments also encompass methods for making and for administering the disclosed compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed compositions including modes of administration through intraocular, intranasal, and intraauricular pathways.

The pharmaceutically effective amount of the ingredients disclosed herein required as a dose will depend on the route of administration and the physical characteristics of the specific human under consideration. The dose can be tailored to achieve a desired effect, but will depend on such factors as weight, diet, concurrent medication and other factors, which those skilled in the medical arts will recognize.

In practicing the methods of the invention, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular ingredients employed, and the specific use for which these ingredients are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods. In non-human animal studies, applications of potential products are commenced at higher dosage levels, with dosage being decreased until the desired effect is no longer achieved or adverse side effects disappear.

The dosage of active ingredient(s) may range broadly, depending upon the desired affects and the therapeutic indication. Typically, dosages of active ingredient(s) may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administrated dose may vary with the severity of a particular medical or physical condition and the route of administration. The severity of a condition may, for example, be evaluated, in part, by standard prognostic evaluation methods. Further, the dose and perhaps dose frequency, may also vary according to the age, body weight, and response of the individual. A program comparable to that discussed above may be used in veterinary medicine.

A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The combined active ingredients in the compositions disclosed herein may be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day. Alternatively, the active ingredients disclosed herein may be administered in the stated amounts continuously by, for example, an intravenous drip. Thus, for a patient weighing 70 kilograms, the preferred daily dose of the total active ingredients would be about 0.0007 mg/kg/day to about 35 mg/kg/day, and more preferable, 0.007 mg/kg/day to about 15 mg/kg/day. Nonetheless, as will be understood by those of skill in the art, in certain situations it may be necessary to administer the active ingredients disclosed herein in amounts that excess, or even far exceed, the above-stated, preferred dosage range to treat effectively and aggressively a desired condition or characteristic.

Ingredients disclosed herein can be evaluated for efficacy and toxicity using known methods. For example, the toxicology of a particular compound or ingredient, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds or ingredients in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds or ingredients disclosed herein, including obesity. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or ingredient in humans.

The active ingredients described above may be used alone or in combination with one another, or in combination with other therapeutic or diagnostic agents. These products can be utilized in vivo or in vitro. The useful dosages and the most useful modes of administration will vary depending upon the age and weight of the consumer, the particular ingredients employed, and the specific use for which these ingredients are employed.

Methods of Use

The compositions described herein may be used for promoting weight loss, increasing energy, increasing metabolic rate, increasing thermogenesis, and/or decreasing food cravings. Thus, in some embodiments, the compositions described herein are administered to a human diagnosed with obesity. In some embodiments, the compositions described herein are administered to a human considered overweight. In some embodiments, weight loss is achieved by a program that includes ingesting the compositions described herein, engaging in a regular exercise program, and having a healthy diet.

The following non-limiting examples are meant to describe the preferred methods of the invention using certain preferred embodiments of the invention. Variations in the details of the particular methods employed and in the precise compositions obtained will undoubtedly be appreciated by those of skill in the art.

EXAMPLES

Example 1

Herbal Supplement Formulation

A tablet is formulated having the ingredients and relative amounts listed in Table 1. The tablet is coated with a suitable coating material such as Opadry Clear YS-1-7006.

TABLE 1

| Ingredient | Amount (% of total tablet weight) |
|---|---|
| Green Tea Extract | 30 |
| Microcrystalline Cellulose NF | 27 |
| Ginger Extract | 15 |
| Caffeine | 10 |
| Maltodextrin M100 | 10 |
| Starch, Corn NF | 5 |
| Magnesium Stearate (Veg. Grade) | 3 |

Example 2

Herbal Supplement Formulation

A tablet is formulated having the ingredients and relative amounts listed in Table 2. The tablet is coated with a suitable coating material such as Opadry Clear YS-1-7006.

TABLE 2

| Ingredient | Amount (% of total tablet weight) |
|---|---|
| Green Tea Extract | 30 |
| Calcium Carbonate Granular 95% (5% Maltodextrin | 15 |
| Microcrystalline Cellulose NF | 15 |
| Caffeine | 10 |
| Maltodextrin M100 | 6 |
| Cocoa Extract | 5 |
| Yerba Mate Extract | 5 |
| Starch, Corn NF | 3 |
| Sodium Starch Glycolate | 3 |
| Silicon Dioxide 50S | 2 |
| Sodium Carboxymethylcellulose | 2 |
| Magnesium Stearate (Veg. Grade) | 2 |
| Hawthorn Berry Powder | 1.8 |
| Ginger Extract | 0.2 |

Example 3

Pharmaceutical Composition

A pharmaceutical composition having the ingredients and relative amounts listed in Table 3 is formulated using a standard wet granulation process to yield a tablet.

TABLE 3

| Ingredient | Amount (% of total tablet weight) |
|---|---|
| Calcium Carbonate, Granular 95% (5% Maltodextrin) | 20 |
| Gingerol | 15 |
| Microcrystalline Cellulose NF | 12 |
| Epigallocatechin-3-gallate | 10 |
| Maltodextrin M100 | 10 |
| Caffeine | 10 |
| Theobromine | 10 |
| Starch, Corn NF | 5 |
| Sodium Starch Glycolate | 3 |
| Silicon Dioxide 50S | 2 |
| Sodium Carboxymethylcellulose | 2 |
| Magnesium Stearate (Veg. Grade) | 1 |

Example 4

Herbal Supplement Formulation

A tablet is formulated having the ingredients and relative amounts listed in Table 4. The tablet is coated with a suitable coating material such as Opadry Clear YS-1-7006.

TABLE 4

| Ingredient | Amount (% of total tablet weight) |
|---|---|
| Green Tea Extract | 20 |
| Calcium Carbonate Granular 95% (5% Maltodextrin | 14 |
| Microcrystalline Cellulose NF | 12 |
| Ginger Extract | 10 |
| Caffeine | 8 |
| Maltodextrin M100 | 6 |
| Cocoa Extract | 5 |
| Yerba Mate Extract | 4 |
| Starch, Corn NF | 3 |
| Sodium Starch Glycolate | 3 |
| Silicon Dioxide 50S | 2 |
| Sodium Carboxymethylcellulose | 2 |
| Magnesium Stearate (Veg. Grade) | 1 |
| Celery Seed Powder | 1 |
| Hawthorn Berry Powder | 1 |
| Parsley Leaf Powder | 1 |
| Marshmallow Root Powder | 1 |
| Fennel Seed Powder | 1 |
| Astragalus Root Powder | 1 |
| Licorice Root Powder | 1 |
| Suma Powder | 1 |
| Cinnamon Extract | 1 |
| Alfalfa Leaf | 1 |

Example 5

Herbal Supplement Formulation

A tablet is formulated having the ingredients and relative amounts listed in Table 5. The tablet is coated with a suitable coating material such as Opadry Clear YS-1-7006.

TABLE 5

| Ingredient | Amount (% of total tablet weight) |
|---|---|
| Ginger Extract | 30 |
| Green Tea Extract | 15 |
| Calcium Carbonate Granular 95% (5% Maltodextrin | 15 |
| Caffeine | 7 |
| Microcrystalline Cellulose NF | 3 |
| Maltodextrin M100 | 3 |
| Cocoa Extract | 3 |
| Yerba Mate Extract | 3 |
| Starch, Corn NF | 3 |
| Sodium Starch Glycolate | 3 |
| Silicon Dioxide 50S | 2 |
| Sodium Carboxymethylcellulose | 2 |
| Magnesium Stearate (Veg. Grade) | 1 |
| Celery Seed Powder | 1 |
| Hawthorn Berry Powder | 1 |
| Parsley Leaf Powder | 1 |
| Marshmallow Root Powder | 1 |
| Fennel Seed Powder | 1 |
| Astragalus Root Powder | 1 |
| Licorice Root Powder | 1 |
| Suma Powder | 1 |
| Cinnamon Extract | 1 |
| Alfalfa Leaf | 1 |

Example 6

Treatment of Obesity

The formulations of Examples 1, 2, 3, 4, or 5 is administered once a day to a human suffering from the condition of obesity and the condition is ameliorated.

Example 7

Weight Loss Program

A human is considered overweight. The overweight human ingests a formulation of Examples 1, 2, 3, 4, or 5 once a day, exercises regularly, and has a diet generally recognized as healthy. The human experiences weight loss in excess of the weight loss that would be experienced had the human not ingested the formulation.

What is claimed is:

1. A tablet useful in affecting weight-loss tablet comprising effective amounts of green tea, ginger, caffeine, cocoa, calcium, yerba maté, hawthorne berry, parsley leaf marshmallow root, fennel seed, astragalus root, licorice root, suma, cinnamon, celery seed, and alfalfa leaf.

2. The tablet of claim 1, wherein between 10% and 40% by weight is green tea, between 5% and 25% by weight is ginger, between 1% and 20% by weight is caffeine, between 1% and 20% by weight is cocoa, between 1% and 20% by weight is yerba maté, between 0.1% and 5% by weight is hawthorne berry, between 0.1% and 5% by weight is parsley leaf, between 0.1% and 5% by weight is marshmallow root, between 0.1% and 5% by weight is fennel seed, between 0.1% and 5% by weight is astragalus root, between 0.1% and 5% by weight is licorice root, between 0.1% and 5% by weight is suma, between 0.1% and 5% by weight is cinnamon, between 0.1% and 5% by weight is celery seed, and between 0.1% and 5% by weight is alfalfa leaf.

3. The tablet of claim 1, wherein the green tea is in the form of a green tea extract and wherein the green tea extract comprises epigallocatechin-3-gallate.

4. The tablet of claim 3, wherein the green tea extract comprises catechins.

5. The tablet of claim 1, wherein the cocoa is in the form of a extract from *Theobroma cacao* seeds.

6. The tablet of claim 2, wherein the green tea is approximately 20% by weight.

7. The tablet of claim 2, wherein the ginger is approximately 10% by weight.

8. The tablet of claim 2, wherein the caffeine is approximately 8% by weight.

9. The tablet of claim 2, wherein the cocoa is approximately 5% by weight.

10. The tablet of claim 2, wherein the yerba mate is approximately 4% by weight.

11. The tablet of claim 2, wherein the hawthorne berry is approximately 1% by weight.

12. The tablet of claim 2, wherein the parsley leaf is approximately 1% by weight.

13. The tablet of claim 2, wherein the marshmallow root is approximately 1% by weight.

14. The tablet of claim 2, wherein the fennel seed is approximately 1% by weight.

15. The tablet of claim 2, wherein the astragalus root is approximately 1% by weight.

16. The tablet of claim 2, wherein the licorice root is approximately 1% by weight.

17. The tablet of claim 2, wherein the suma is approximately 1% by weight.

18. The tablet of claim 2, wherein the cinnamon is approximately 1% by weight.

19. The tablet of claim 2, wherein the celery seed is approximately 1% by weight.

20. The tablet of claim 2, wherein the alfalfa leaf is approximately 1% by weight.

21. The tablet of claim 2, wherein the approximately 20% by weight is green tea, approximately 10% by weight is ginger, approximately 8% by weight is caffeine, approximately 5% by weight is cocoa, approximately 4% by weight is yerba maté, approximately 1% by weight is hawthorne berry, approximately 1% by weight is parsley leaf, approximately 1% by weight is marshmallow root, approximately 1% by weight is fennel seed, approximately 1% by weight is astragalus root, approximately 1% by weight is licorice root, approximately 1% by weight is suma, approximately 1% by weight is cinnamon, approximately 1% by weight is celery seed, and approximately 1% by weight is alfalfa leaf.

* * * * *